United States Patent
Takayama

(10) Patent No.: US 9,957,262 B2
(45) Date of Patent: May 1, 2018

(54) OPIOID ANALGESIC

(71) Applicant: NATIONAL UNIVERSITY CORPORATION CHIBA UNIVERSITY, Chiba (JP)

(72) Inventor: Hiromitsu Takayama, Chiba (JP)

(73) Assignee: National University Corporation Chiba University, Chiba (JP)

(*) Notice: Subject to any disclaimer, the term of this patent is extended or adjusted under 35 U.S.C. 154(b) by 256 days.

(21) Appl. No.: 15/032,070

(22) PCT Filed: Oct. 28, 2014

(86) PCT No.: PCT/JP2014/078632
§ 371 (c)(1),
(2) Date: Aug. 8, 2016

(87) PCT Pub. No.: WO2015/064573
PCT Pub. Date: May 7, 2015

(65) Prior Publication Data
US 2016/0340352 A1 Nov. 24, 2016

(30) Foreign Application Priority Data
Oct. 29, 2013 (JP) ................. 2013-224412

(51) Int. Cl.
C07D 491/22 (2006.01)
A61K 31/4375 (2006.01)
C07D 455/00 (2006.01)

(52) U.S. Cl.
CPC ........ *C07D 455/00* (2013.01); *A61K 31/4375* (2013.01); *C07D 491/22* (2013.01)

(58) Field of Classification Search
None
See application file for complete search history.

(56) References Cited

U.S. PATENT DOCUMENTS
2009/0221623 A1 9/2009 Takayama et al.

FOREIGN PATENT DOCUMENTS
WO 2007110637 A1 10/2007

OTHER PUBLICATIONS

Duwiejua et al., "Pseudo-akuammigine, an alkaloid from Picralima nitida seeds, has anti-inflammatory and analgesic actions in rats," Journal of Ethnopharmacology, vol. 81, 2002, pp. 73-79.

Matsumoto et al., "Antinociceptive effect of 7-hydroxymitragynine in mice: Discovery of an orally active opioid analgesic from the Thai medicinal herb Mitragyna speciosa," Life Sciences, vol. 74, 2004, pp. 2143-2155.

Takayama et al., "New Procedure to Mask the 2,3-π Bond of the Indole Necleus and Its Application to the Preparation of Potent Opioid Receptor Agonists with a Corynanthe Skeleton," Organic Letters, vol. 8, No. 25, 2006, pp. 5705-5708.

Takayama et al., "Studies on the Synthesis and Opioid Agonistic Activities of Mitragynine-Related Indole Alkaloids: Discovery of Opioid Agonists Structurally Different from Other Opioid Ligands," Journal of Medicinal Chemistry, vol. 45, No. 9, 2002, pp. 1949-1956.

*Primary Examiner* — Gigi Huang
(74) *Attorney, Agent, or Firm* — Kilyk & Bowersox, P.L.L.C.

(57) ABSTRACT

Provided are a compound represented by formula (I) or (II), a salt thereof, or solvates of the compound and salt, having an analgesic effect and high metabolic stability. Further provided are the following: an analgesic obtained from the compound, a salt thereof, or solvates of the compound and salt; a pharmaceutical composition containing the compound, a salt thereof, or solvates of the compound and salt; an analgesic treatment method using the compound, a salt thereof, or solvates of the compound and salt; and a use of the compound, a salt thereof, or solvates of the compound and salt, in the production of an analgesic composition.

5 Claims, 1 Drawing Sheet

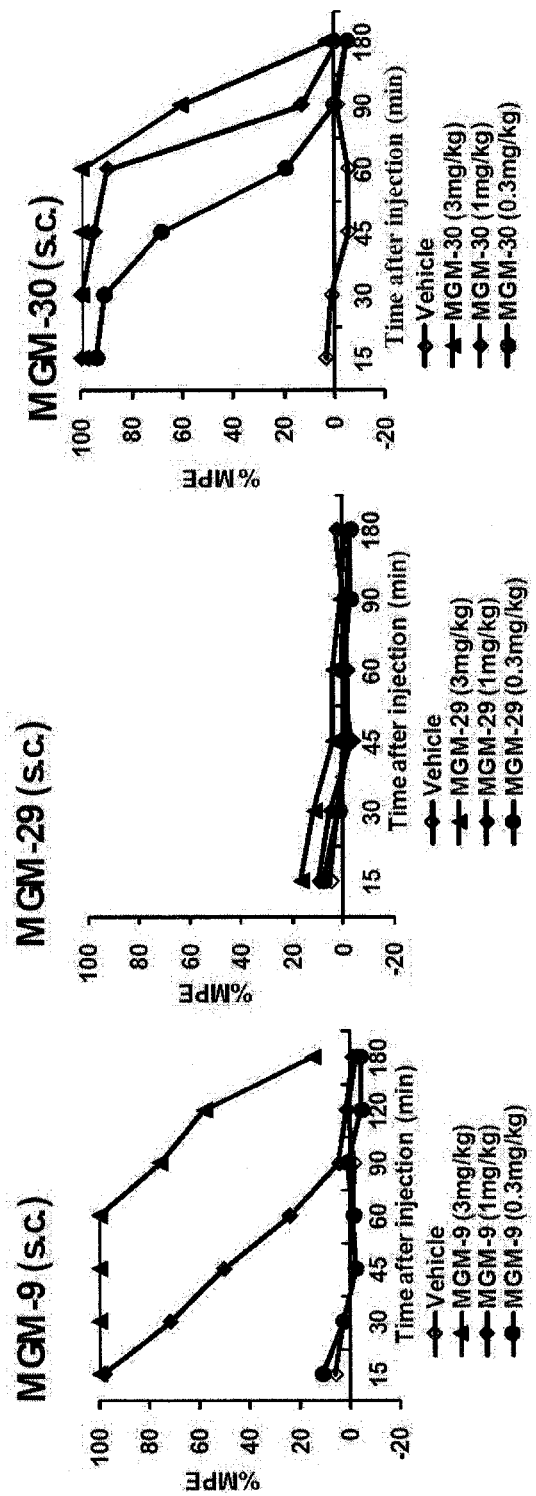

OPIOID ANALGESIC

TECHNICAL FIELD

The present invention relates to a compound having an analgesic action and a pharmaceutical application thereof. More specifically, the present invention relates to a mitragynine derivative compound and a pharmaceutical application thereof.

BACKGROUND ART

Morphine is an analgesic indispensable for an improvement in quality of life (QOL) of a patient with cancer pain. However, morphine has problems of, for example, having low bioavailability and causing various side effects, such as formation of analgesic resistance and physical or psychological dependence due to continued use, nausea and vomiting, constipation, sleepiness, and respiratory depression. Therefore, the advent of an ideal analgesic serving as a substitute for morphine has long been strongly demanded. In search of more excellent analgesics, investigations on synthetic analgesics were started with chemical modification of a morphine molecule in the 1920s, and synthesis and pharmacological activity evaluation of a large number of compounds are still performed today. However, there are few examples of development of an effective opioid analgesic substance serving as a substitute for a morphine skeleton. Meanwhile, investigations on expression of an analgesic action of morphine have also been greatly advanced in recent years, and efforts to elucidate a molecular mechanism of analgesia have been made on the basis of, for example, classification of opioid receptors (δ-, μ-, and κ-receptors) and determination of amino acid sequences thereof. However, there are complicated interactions among those three kinds of receptors, and a logical methodology for separating an analgesic property from side effects, such as a narcotic property, has not yet been established.

The present inventor and colleagues found that an alkaloid contained in a rubiaceous plant *Mitragyna speciosa*, which had been used as a substitute for morphine in Thailand and Malaysia, had a potent analgesic action, and then achieved isolation and efficient asymmetric total synthesis of 7-hydroxymitragynine (sometimes referred to as 7-hydroxymitragynine), an indole alkaloid that was a trace ingredient considered to be a main active principle of the alkaloid (Non Patent Literature 1). In addition, the present inventor and colleagues reported that 7-hydroxymitragynine inhibited contraction induced by electrical stimulation in guinea pig small intestine via opioid receptors (Non Patent Literature 1), and exhibited a remarkable antinociceptive action by subcutaneous administration or oral administration in a tail-flick test or a hot-plate test using mice (Non Patent Literature 2). Further, the present inventor and colleagues synthesized derivatives of 7-hydroxymitragynine and mitragynine, and reported derivative compounds exhibiting more potent analgesic actions than that of morphine and having reduced side effects (Patent Literatures 1 to 3 and Non Patent Literature 3).

CITATION LIST

Patent Literature

[PTL 1] WO 2009/069764 A1
[PTL 2] US 2009/0221623 A1
[PTL 3] US 2012/0276195 A1

Non Patent Literature

[NPL 1] Takayama H. et al., "Journal of Medicinal Chemistry", 2002, Vol. 45, No. 9, p. 1949-1956
[NPL 2] Matsumoto K. et al., "Life Sciences", 2004, Vol. 74, No. 17, p. 2143-2155
[NPL 3] Takayama H. et al., "Organic Letters", 2006, Vol. 8, No. 25, p. 5705-5708

SUMMARY OF INVENTION

Problem to be Solved by the Invention

An object of the present invention is to provide a compound having a potent analgesic action, which serves as a substitute for morphine, a pharmaceutical composition and an analgesic each containing the compound as an active ingredient, an analgesic treatment method comprising using the compound, and a use of the compound in analgesic treatment.

Means for Solving Problem

The inventor of the present invention has made extensive investigations in order to achieve the above-mentioned object, and has found that a novel derivative of mitragynine exhibits a potent analgesic action and also exhibits high stability in a pharmacokinetic study using human and rat liver microsomes. The present invention has been achieved on the basis of those findings.

That is, the present invention relates to the following.
(1) An analgesic, comprising a compound represented by the following formula (I) or the following formula (II) or a salt thereof, or a solvate thereof.

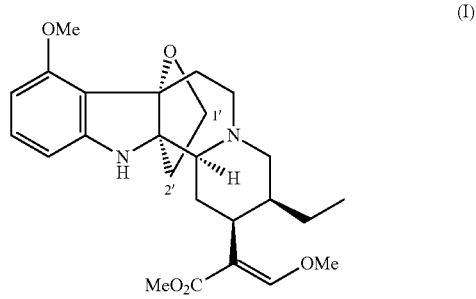

(I)

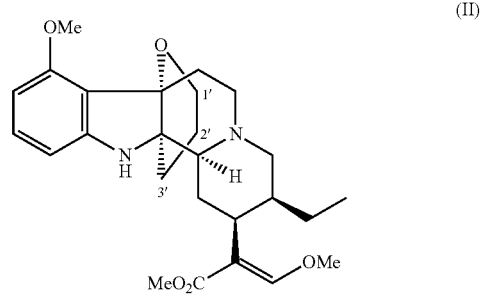

(II)

(2) A pharmaceutical composition, comprising an effective amount of a compound represented by the formula (I) or the formula (II) or a salt thereof, or a solvate thereof as an active ingredient.
(3) The pharmaceutical composition according to the above-mentioned item (2), wherein the pharmaceutical composition is a pharmaceutical composition for analgesic treatment.
(4) Use of a compound represented by the formula (I) or the formula (II) or a salt thereof, or a solvate thereof for manufacture of a pharmaceutical composition.
(5) The use according to the above-mentioned item (4), wherein the pharmaceutical composition is a pharmaceutical composition for analgesic treatment.
(6) A compound represented by the formula (I) or a salt thereof, or a solvate thereof.
(7) A compound represented by the formula (II) or a salt thereof, or a solvate thereof.
(8) A method of inducing a therapeutic effect in a subject, comprising administering an effective amount of a compound represented by the formula (I) or the formula (II) or a salt thereof, or a solvate thereof to the subject.
(9) The method according to the above-mentioned item (8), wherein the therapeutic effect is an analgesic effect.

Advantageous Effects of Invention

According to the present invention, the compound having an analgesic action, the pharmaceutical composition and the analgesic each containing the compound as an active ingredient, the analgesic treatment method comprising using the compound, and the use of the compound in analgesic treatment and production of an analgesic can be provided.

The compound according to the present invention exhibits a more potent analgesic action than that of morphine. Therefore, the compound according to the present invention can be effectively used as an analgesic serving as a substitute for morphine in various analgesic treatments. In addition, the compound according to the present invention exhibited high stability in a pharmacokinetic study using human liver microsome, and hence is considered to exhibit effects of high stability in a living body as well and a long duration of action. The compound according to the present invention has such features, and hence is highly useful in analgesic treatment.

BRIEF DESCRIPTION OF DRAWINGS

FIG. 1 shows results of analgesic actions of test compounds, MGM-30 and MGM-29, in a mouse tail-flick test, which are administered by subcutaneous administration (S.C.). The results of the test are represented by dose-response curves. A similar test was performed by using MGM-9, which was a known mitragynine derivative compound exhibiting a more potent analgesic action than that of morphine, for comparison. In addition, a similar test was performed by using a vehicle as a negative control. The analgesic action of each compound was quantified by using a percentage of maximum possible effect (% MPE). % MPE was calculated from the following equation: % MPE=[(Post-drug latency−Pre-drug latency)/(Cut-off time−Pre-drug latency)]×100. The abscissa axis of FIG. 1 indicates a time after the administration of each compound (time after injection (min)).

DETAILED DESCRIPTION OF THE INVENTION

The present invention relates to a compound represented by the following formula (I) or the following formula (II).

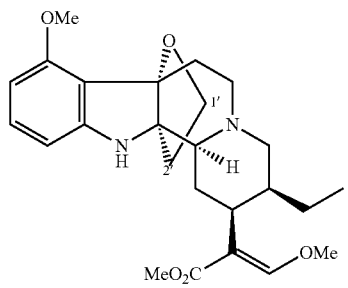

(I)

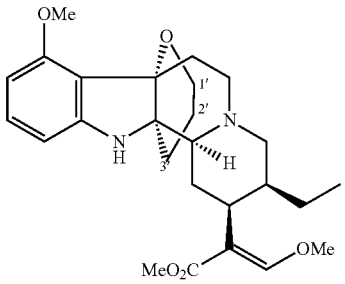

(II)

Herein, the compound represented by the formula (I) is sometimes referred to as MGM-30, and the compound represented by the formula (II) is sometimes referred to as MGM-29.

The compound according to the present invention may be in the form of a salt. The salt is preferably a pharmacologically acceptable salt, and examples thereof include salts with inorganic bases, salts with organic bases, salts with inorganic acids, salts with organic acids, and salts with basic or acidic amino acids. The term "pharmacologically acceptable salt" is used in the same meaning as the term "pharmaceutically acceptable salt," and means a salt that may be used as a pharmaceutical product. Specifically, suitable examples of the salts with inorganic bases, the salts with organic bases, and the salts with basic amino acids may include: salts with inorganic bases, such as sodium, potassium, magnesium, calcium, and aluminum; salts with organic bases, such as methylamine, ethylamine, and ethanolamine; salts with basic amino acids, such as lysine and ornithine; and an ammonium salt. Suitable examples of the salts with inorganic acids, the salts with organic acids, and the salts with acidic amino acids may include: salts with mineral acids, such as hydrochloric acid, hydrobromic acid, hydroiodic acid, sulfuric acid, nitric acid, and phosphoric acid; salts with organic acids, such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; and salts with acidic amino acids, such as aspartic acid and glutamic acid. Among the salts, a sodium salt, a potassium salt, a hydrochloric acid salt, or the like is preferable.

In addition, the compound and the salt thereof according to the present invention may each be in the form of any of various solvates. The solvate is preferably a pharmacologically acceptable solvate, and examples thereof may include a monohydrate, a dihydrate, a monosolvate, and a disolvate. Further, the compound and the salt thereof according to the present invention may be crystal polymorphs.

The compound according to the present invention has a potent analgesic action. Specifically, in a mouse tail-flick test, which is well known as an evaluation method for an analgesic effect, the compound represented by the formula (I) exhibited a potent analgesic action in a dose-dependent manner by subcutaneous administration. The analgesic action of the compound according to the present invention was approximately 3-fold as potent as the analgesic action of a known mitragynine derivative compound represented by the following formula (III), which exhibited a more potent analgesic action than that of morphine (see Example 2). In addition, the compound represented by the formula (II) exhibited an analgesic action, although the action was determinative.

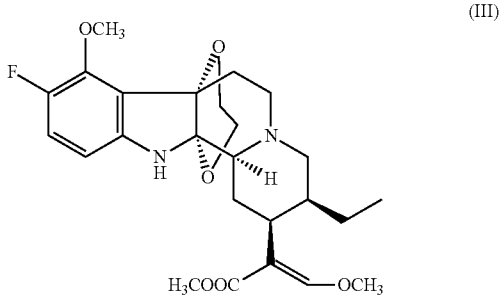

(III)

The compound according to the present invention was found to have a high affinity for human µ-opioid receptors. Thus, it can be considered that the analgesic action of the compound resulted from its action as a µ-opioid receptor agonist. Specifically, the compound represented by the formula (I) exhibited a binding affinity for human µ-opioid receptors about 30-fold as potent as that of the compound represented by the formula (III) (Example 3). In addition, the compound represented by the formula (II) exhibited a binding affinity for human µ-opioid receptors comparable to that of the compound represented by the formula (III).

The compound according to the present invention shows high metabolic stability, which is a feature thereof. Specifically, in an in vitro metabolic stability test using liver microsome, each of the compound represented by the formula (I) and the compound represented by the formula (II) exhibited remarkably high metabolic stability as compared to that of the compound represented by the formula (III) (Example 3). The metabolic stability is an important factor for the expression of drug efficacy in a body. It can be considered that a drug having higher metabolic stability has usefulness such as the expression of drug efficacy at lower dosage and a longer duration of drug efficacy.

The compound according to the present invention is a mitragynine derivative compound, and may be produced by synthesis using mitragynine as a start material.

The synthesis of the compound represented by the formula (I) may be carried out, for example, by subjecting mitragynine and 2-iodoethanol to a reaction in the presence of iodosobenzene diacetate (hereinafter abbreviated as IBDA), which is an oxidizing agent containing iodine, and subjecting the resultant iodinated form to radical cyclization by addition of triethylborane (hereinafter abbreviated as Et₃B), which is a radical initiator (see Example 1). In addition, the synthesis of the compound represented by the formula (II) may be carried out, for example, by subjecting mitragynine and 3-iodopropanol to a reaction in the presence of IBDA, and subjecting the resultant iodinated form to radical cyclization by addition of Et₃B (see Example 1). Mitragynine may be obtained by isolation from nature or chemical synthesis (Ponglux D. et al., "Planta Medica", 1994, Vol. 60, No. 6, p. 580-581; and Takayama H. et al., "Tetrahedron Letters", 1995, Vol. 36, No. 51, p. 9337-9340).

The compound according to the present invention can be used in the production of an analgesic. For example, in the present invention, an analgesic comprising the compound according to the present invention can be provided.

The compound according to the present invention can also be used in the production of a pharmaceutical composition. That is, in the present invention, a pharmaceutical composition containing an effective amount of the compound according to the present invention as an active ingredient can be provided. The pharmaceutical composition according to the present invention may contain one or a combination of both of the compounds according to the present invention. In addition, the pharmaceutical composition according to the present invention may further contain, in addition to the compound according to the present invention, a pharmaceutical agent necessary for treatment.

The pharmaceutical composition according to the present invention can be preferably used as a pharmaceutical composition for analgesic treatment. That is, in the present invention, a pharmaceutical composition for analgesic treatment, containing an effective amount of the compound according to the present invention as an active ingredient, can be provided. The pharmaceutical composition for analgesic treatment according to the present invention may contain one or a combination of both of the compounds according to the present invention. In addition, the pharmaceutical composition according to the present invention may further contain, in addition to the compound according to the present invention, any other pharmaceutical agent having an analgesic effect.

Further, the compound according to the present invention can be used in a method of inducing a therapeutic effect in a subject, the method including administering an effective amount of the compound to the subject. The compound according to the present invention has a more potent analgesic action than that of morphine, and hence can be effectively used as an analgesic serving as a substitute for morphine in various analgesic treatments. In the method according to the present invention, the compound according to the present invention is preferably administered to, for example, a subject in need of analgesic treatment, specifically a subject with pain.

The term "analgesia" as used herein means the alleviation or removal of pain.

The term "pain" means an unpleasant sensory and emotional experience associated with actual or potential tissue damage, or described in terms of such damage. The pain includes cancerous pain, inflammatory pain, neuropathic pain, postoperative pain, and idiopathic pain that is pain of unknown cause, for example, phantom limb pain. More specifically, the pain may be exemplified by pain due to cancer diseases, herpesvirus infection, human immunodeficiency virus infection, diabetes, hypothyroidism, uremia, causalgia, peripheral nerve trauma, plexus avulsion, dismember, and vasculitis.

The term "treatment" as used herein means the alleviation of the severity and/or frequency of a symptom. Accordingly, the "analgesic treatment" means the alleviation of the severity and/or frequency of pain in an individual.

The term "subject" is used interchangeably with the term "living body" or the term "patient".

Each of the pharmaceutical composition and the analgesic according to the present invention contains the compound according to the present invention as an active ingredient, and may also contain, as necessary, a pharmaceutical carrier generally used in the production of a pharmaceutical product. Examples of the pharmaceutical carrier may include an excipient, a disintegrant, a diluent, a lubricant, a flavoring agent, a colorant, a sweetening agent, a taste-masking agent, a suspending agent, a wetting agent, an emulsifier, a dispersant, an adjuvant, an antiseptic, a buffering agent, a binder, a stabilizing agent, and a coating agent.

Any of systemic administration or local administration may be selected as an administration route. In this case, an appropriate administration route is selected depending on a disease, a symptom, or the like. The analgesic according to the present invention may be administered through any of an oral route and a parenteral route. Examples of the parenteral route may include subcutaneous administration, intradermal administration, and intramuscular administration as well as general intravenous administration and intraarterial administration. Further, transmucosal administration or transdermal administration may be carried out.

A dosage form is not particularly limited, and there may be adopted various dosage forms, for example, a tablet, a capsule, a powder, a granule, a pill, a liquid, an emulsion, a suspension, a solution, a spirit, a syrup, an extract, and an elixir for oral administration. A parenteral formulation may be exemplified by, but not limited to: injections, such as a subcutaneous injection, an intravenous injection, an intramuscular injection, and an intraperitoneal injection; a patch, an ointment, or a lotion for transdermal administration; a sublingual formulation or a buccal patch for buccal administration; an aerosol formulation for transnasal administration; and a suppository. In addition, the dosage form may be a sustained-release dosage form or a controlled-release dosage form. Those formulations may each be produced by a known method generally used in a formulation process.

In the case of preparing a solid formulation for oral administration, a tablet, a coated tablet, a granule, a powder, a capsule, or the like may be produced by using a conventional method after adding an excipient, and as necessary, a binder, a disintegrant, a lubricant, a colorant, a taste-masking agent, an odor-masking agent, or the like to the compound according to the present invention. An additive generally used in the art may be adopted as such additive. Examples of the excipient may include lactose, saccharose, sodium chloride, glucose, starch, calcium carbonate, kaolin, microcrystalline cellulose, and silicic acid. Examples of the binder may include water, ethanol, propanol, simple syrup, dextrose in water, starch in water, gelatin in water, carboxymethyl cellulose, hydroxypropyl cellulose, hydroxypropyl starch, methyl cellulose, ethyl cellulose, shellac, calcium phosphate, and polyvinylpyrrolidone. Examples of the disintegrant may include dry starch, sodium alginate, powdered agar, sodium bicarbonate, calcium carbonate, sodium lauryl sulfate, stearic acid monoglyceride, and lactose. Examples of the lubricant may include purified talc, a stearate, borax, and polyethylene glycol. Examples of the taste-masking agent may include saccharose, orange peel, citric acid, and tartaric acid.

In the case of preparing a liquid formulation for oral administration, an oral liquid, a syrup, an elixir, or the like may be produced by using a conventional method after adding a taste-masking agent, a buffering agent, a stabilizing agent, an odor-masking agent, or the like to the compound according to the present invention. In this case, the taste-masking agent may be any of the agents listed above, an example of the buffering agent may be sodium citrate, and examples of the stabilizing agent may include tragacanth, gum arabic, and gelatin.

In the case of preparing an injection, subcutaneous, intramuscular, and intravenous injections may each be produced by using a conventional method after adding a pH adjustor, a buffering agent, a stabilizing agent, a tonicity agent, a local anesthetic, or the like to the compound according to the present invention. Examples of the pH adjustor and the buffering agent in this case may include sodium citrate, sodium acetate, and sodium phosphate. Examples of the stabilizing agent may include sodium pyrosulfite, ethylenediaminetetraacetic acid (EDTA), thioglycolic acid, and thiolactic acid. Examples of the local anesthetic may include procaine hydrochloride and lidocaine hydrochloride. Examples of the tonicity agent may include sodium chloride and glucose.

In the case of preparing a suppository, the suppository may be produced by using a conventional method after adding a known carrier for formulation, for example, polyethylene glycol, lanolin, cacao butter, or a fatty acid triglyceride, to the compound according to the present invention, and further adding a surfactant, for example, Tween®, as necessary.

In the case of preparing an ointment, the compound according to the present invention is blended with, as necessary, a base, a stabilizing agent, a wetting agent, a preservative, or the like generally used, followed by mixing and formulation by a conventional method. Examples of the base may include liquid paraffin, white petrolatum, white beeswax, octyldodecyl alcohol, and paraffin. Examples of the preservative may include methyl paraoxybenzoate, ethyl paraoxybenzoate, and propyl paraoxybenzoate. A cream, a gel, a paste, or the like may also be formulated in the same way.

In the case of producing a patch, the ointment, the cream, the gel, the paste, or the like may be applied onto a general support by a conventional method. The support is suitably a woven fabric or a nonwoven fabric formed of cotton, staple fibers, or chemical fibers, or a film or a foam sheet formed of soft vinyl chloride, polyethylene, polyurethane, or the like.

A dose range is not particularly limited, and is appropriately selected depending on, for example, the effectiveness of an ingredient contained, an administration mode, an administration route, the kind of a disease, the characteristics of a subject (e.g., body weight, age, medical conditions, and whether or not any other pharmaceutical is used), and judgment by a doctor in attendance. In general, it is preferable that an appropriate dose fall within a range of, for example, from about 0.01 µg to about 100 mg, preferably from about 0.1 µg to about 1 mg per kg of body weight of a subject. However, such dose may be changed through general routine experimentation for optimization well known in the art. The dosage may be administered in single or divided doses per day. Alternatively, there may be adopted such an administration mode that administration is performed at the time of the development of pain.

The present invention is hereinafter described more specifically by way of Examples, but is in no way limited to the following Examples.

Example 1

MGM-30 and MGM-29 were each synthesized by using mitragynine as a start material. Details thereof are described below.

The mitragynine serving as the start material was obtained from *Mitragyna speciosa* according to a method described in each of the previous reports (Ponglux D. et al., "Planta Medica", 1994, Vol. 60, No. 6, p. 580-581; and Takayama H. et al, "Tetrahedron Letters", 1995, Vol. 36, No. 51, p. 9337-9340).

1. Synthesis of MGM-30

MGM-30 was synthesized by converting mitragynine into its iodinated form and then subjecting the iodinated form to radical cyclization.

1-1. Conversion of Mitragynine into Iodinated Form (Formula (IV))

Mitragynine (100.0 mg, 0.251 mmol) was dissolved in 2-iodoethanol (0.66 mL), and CH$_3$CN (1.0 mL) was added to the solution. Under ice cooling, IBDA (80 mg, 0.248 mmol) was added in three portions, and the mixture was stirred at room temperature for 1 hour and 30 minutes in an argon atmosphere. The reaction liquid was poured into an ice-cold saturated sodium bicarbonate aqueous solution and extracted three times with ether. The extracted organic layers were washed with brine and dried over sodium sulfate, followed by the evaporation of the solvent under reduced pressure and vacuum drying. Thus, a residue was obtained. The resultant residue was purified by medium pressure liquid chromatography (aminosilica gel, 30% ethyl acetate/n-hexane) to obtain an iodinated form represented by the following formula (IV) (37.6 mg, 34% yield).

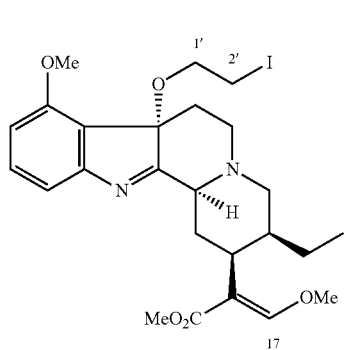

(IV)

Analysis data of the product are shown below. $^1$H-NMR (400 MHz, CDCl$_3$) δ [ppm]: 7.45 (1H, s, H-17), 7.32 (1H, dd, J=8.0, 8.0 Hz, H-11), 7.22 (1H, d, J=7.5 Hz, H-12), 6.75 (1H, d, J=8.2 Hz, H-10), 3.86 (3H, s, 9-OCH$_3$), 3.81 (3H, s, 17-OCH$_3$), 3.70 (3H, s, 22-OCH$_3$), 3.23-3.08 (5H, overlapped, H$_2$-1', H-3, H-5, and H-15), 3.02 (2H, m, H$_2$-2'), 2.91-2.77 (2H, overlapped) and 2.73 (1H, ddd, J=14.1, 2.4, 2.0 Hz) (H-6, H-14, and H-21), 2.60 (1H, m, H-5), 2.49 (1H, dd, J=11.4, 2.5 Hz, H-21), 1.88 (1H, m, H-14), 1.75-1.56 (3H, overlapped, H-6, H-19, and H-20), 1.24 (1H, m, H-19), 0.82 (3H, dd, J=7.4, 7.4 Hz, H$_3$-18). $^{13}$C-NMR (100 MHz, CDCl$_3$) δ [ppm]: 183.7 (C-2), 169.3 (C-22), 160.7 (C-17), 156.5 (C-9), 155.4 (C-13), 131.2 (C-11), 122.7 (C-8), 114.4 (C-12), 111.2 (C-16), 108.9 (C-10), 86.2 (C-7), 65.3 (C-1'), 62.0 (17-OCH$_3$), 61.8 (C-3), 58.1 (C-21), 55.5 (9-OCH$_3$), 51.3 (22-OCH$_3$), 50.3 (C-5), 40.5 (C-20), 39.3 (C-15), 35.1 (C-6), 26.0 (C-14), 18.9 (C-19), 12.8 (C-18), 3.0 (C-2').

UV (MeOH) λ$_{max}$: 303.5, 240.5 (sh), 221.5 nm.

1-2. Synthesis of MGM-30 by Radical Cyclization of the Iodinated Form Represented by Formula (IV)

The iodinated form (37.6 mg, 0.066 mmol) represented by the formula (IV) was dissolved in benzene (1.5 mL), followed by nitrogen purging. Then, the solution was stirred for 10 minutes in a nitrogen atmosphere. Under ice cooling, Et$_3$B (1.04 mol/L in n-hexane, 0.62 mL, 0.645 mmol) was slowly added, and the mixture was stirred at room temperature for 45 minutes while maintaining the syringe needle being inserted, and then stirred after taking out the syringe needle for 3 hours and 15 minutes. When Et$_3$B (1.04 mol/L in n-hexane, 0.62 mL, 0.645 mmol) was further added, a solid was precipitated, and hence benzene (1.0 mL) was added. After that, the solvent was evaporated with nitrogen, and the residue was left to stand at room temperature overnight. The reaction liquid was poured into an ice-cold saturated sodium bicarbonate aqueous solution and extracted three times with chloroform. The extracted organic layers were washed with brine and dried over sodium sulfate, followed by the evaporation of the solvent under reduced pressure and vacuum drying. Thus, a residue was obtained. The resultant residue was purified by medium pressure liquid chromatography (aminosilica gel, 30% ethyl acetate/n-hexane) to obtain MGM-30 (20.8 mg, 71% yield).

Analysis data of the product are shown below. $^1$H-NMR (400 MHz, CDCl$_3$) δ [ppm]: 7.42 (1H, s, H-17), 7.02 (1H, dd, J=8.1, 8.1 Hz, H-11), 6.31 (1H, d, J=7.7 Hz) and 6.30 (1H, d, J=8.2 Hz) (H-10 and H-12), 3.95 (1H, ddd, J=7.9, 7.9, 7.9 Hz, H-1'), 3.82 (3H, s, 9-OCH$_3$), 3.81 (3H, s, 17-OCH$_3$), 3.70 (3H, s, 22-OCH$_3$), 3.78 (1H, ddd, J=8.4, 8.4, 4.6 Hz, H-1'), 2.97-2.89 (2H, overlapped, H-15 and H-21), 2.56-2.43 (3H, overlapped), 2.18-2.02 (3H, overlapped), 1.95-1.56 (6H, overlapped), 1.26 (1H, m, H-19), 0.83 (3H, dd, J=7.3, 7.3 Hz, H$_3$-18). $^{13}$C-NMR (100 MHz, CDCl$_3$) δ [ppm]: 169.1 (C-22), 160.3 (C-17), 157.5 (C-9), 149.5 (C-13), 129.8 (C-11), 119.0 (C-8), 111.8 (C-16), 104.9 (C-12), 102.2 (C-10), 88.5 (C-7), 72.1 (C-2), 67.0 (C-3), 65.9 (C-2'), 61.7 (17-OCH$_3$), 58.8 (C-21), 55.4 (9-OCH$_3$), 51.3 (22-OCH$_3$), 50.9 (C-5), 40.7 (C-15), 40.2 (C-20), 39.9 (C-1'), 31.4 (C-6), 26.0 (C-14), 19.0 (C-19), 13.0 (C-18).

UV (MeOH) λ$_{max}$: 290.5, 239.0, 214.0 nm.

2. Synthesis of MGM-29

MGM-29 was synthesized by converting mitragynine into its iodinated form and then subjecting the iodinated form to radical cyclization.

2-1. Conversion of Mitragynine into Iodinated Form (Formula (V))

Mitragynine (50.0 mg, 0.126 mmol) was dissolved in 3-iodopropanol (0.33 mL), and acetonitrile (CH$_3$CN, 0.5 mL) was added to the solution. Under ice cooling, IBDA (40.5 mg, 0.126 mmol) was added in four portions at intervals of 4 minutes, and the mixture was stirred at room temperature for 1 hour in an argon atmosphere. The reaction liquid was poured into an ice-cold saturated sodium bicarbonate aqueous solution and extracted three times with ether. The extracted organic layers were washed with brine and dried over sodium sulfate, followed by evaporation of the solvent under reduced pressure and vacuum drying. Thus, a residue was obtained. The resultant residue was purified by medium pressure liquid chromatography (aminosilica gel, 30% ethyl acetate/n-hexane) to obtain an iodinated form represented by the following formula (V) (31.9 mg, 46% yield).

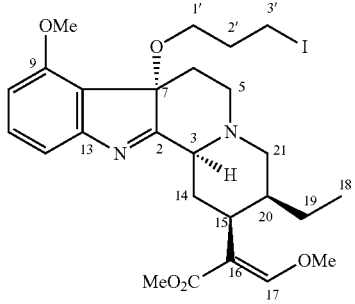

(V)

Analysis data of the product are shown below. $^1$H-NMR (400 MHz, CDCl$_3$) δ [ppm]: 7.45 (1H, s, H-17), 7.32 (1H, dd, J=8.0, 8.0 Hz, H-11), 7.24 (1H, d, J=7.6 Hz, H-12), 6.75 (1H, d, J=8.1 Hz, H-10), 3.87 (3H, s, 9-OCH$_3$), 3.81 (3H, s, 17-OCH$_3$), 3.71 (3H, s, 22-OCH$_3$), 3.29 (2H, m, H$_2$-1'), 3.05-2.98 (3H, overlapped, H-3, H-5, and H-15), 2.93 (2H, dd, J=5.3, 5.3 Hz, H$_2$-3'), 2.89-2.70 (3H, overlapped, H-6, H-14, and H-21), 2.59 (1H, m, H-5), 2.45 (1H, dd, J=11.2, 2.6 Hz, H-21), 2.08-1.88 (3H, overlapped, H-14 and H$_2$-2'), 1.74-1.56 (3H, overlapped, H-6, H-19, and H-20), 1.23 (1H, m, H-19), 0.82 (3H, dd, J=7.2, 7.2 Hz, H$_3$-18).

$^{13}$C-NMR (100 MHz, CDCl$_3$) δ [ppm]: 184.0 (C-2), 169.3 (C-22), 160.7 (C-17), 156.5 (C-9), 155.5 (C-13), 130.9 (C-11), 123.0 (C-8), 114.3 (C-12), 111.2 (C-16), 108.8 (C-10), 86.1 (C-7), 63.2 (C-1'), 62.2 (17-OCH$_3$), 61.8 (C-3), 58.1 (C-21), 55.4 (9-OCH$_3$), 51.3 (22-OCH$_3$), 50.3 (C-5), 40.5 (C-20), 39.3 (C-15), 35.2 (C-6), 33.7 (C-2'), 25.9 (C-14), 18.9 (C-19), 12.8 (C-18), 3.7 (C-3').

UV (MeOH) $\lambda_{max}$: 301.0, 245.5 (sh), 221.5 nm.

CD (0.151 mM, MeOH, 24° C.), λ nm (De): 345 (0), 309 (+2.8), 290 (0), 281 (−0.8), 275 (0), 258 (+4.8), 242 (0), 221 (−9.4), 210 (0). EI-MS (%) m/z: 582 (M$^+$, 41), 397 (100).

2-2. Synthesis of MGM-29 by Radical Cyclization of Iodinated Form Represented by Formula (V)

The iodinated form (31.9 mg, 0.055 mmol) represented by the formula (V) was dissolved in benzene (1.5 mL), followed by nitrogen purging. Then, the solution was stirred for 30 minutes in a nitrogen atmosphere. Et$_3$B (1.04 mol/L in n-hexane, 0.53 mL, 0.541 mmol) was slowly added, and the mixture was stirred at room temperature for 1 hour while maintaining the syringe needle being inserted. Et$_3$B (1.04 mol/L in n-hexane, 0.53 mL, 0.541 mmol) was further added, and the mixture was stirred at room temperature for 20 hours after taking out the syringe needle. The reaction liquid was poured into an ice-cold saturated sodium bicarbonate aqueous solution and extracted three times with chloroform. The extracted organic layers were washed with brine and dried over sodium sulfate, followed by the evaporation of the solvent under reduced pressure and vacuum drying. Thus, a residue was obtained. The resultant residue was purified by medium pressure liquid chromatography (aminosilica gel, 30% ethyl acetate/n-hexane) to obtain MGM-29 (14.0 mg, 56% yield).

Analysis data of the product are shown below. $^1$H-NMR (400 MHz, CDCl$_3$) δ [ppm]: 7.43 (1H, s, H-17), 7.04 (1H, dd, J=8.0, 8.0 Hz, H-11), 6.36 (1H, d, J=7.3 Hz, H-10) and 6.34 (1H, d, J=7.7 Hz, H-12), 3.89 (1H, m, H-1'), 3.84 (3H, s, 9-OCH$_3$), 3.81 (3H, s, 17-OCH$_3$), 3.72 (3H, s, 22-OCH$_3$), 3.62 (1H, ddd, J=12.9, 12.9, 2.2 Hz, H-1'), 2.97 (1H, br-d, J=12.5 Hz, H-21), 2.94 (1H, ddd, J=13.5, 3.6, 3.6 Hz, H-15), 2.51-2.32 (3H, overlapped, H$_2$-5 and H-6), 2.27 (1H, dd, J=11.5, 2.6 Hz, H-21), 2.17 (1H, br-d, J=10.8 Hz, H-3), 1.99-1.70 (5H, overlapped, H$_2$-14, H-19, H-2', and H-3'), 1.65 (1H, br-d, J=12.4 Hz, H-6), 1.55 (1H, m, H-20), 1.54 (1H, ddd, J=13.5, 13.5, 4.2 Hz, H-3'), 1.34 (1H, m, H-2'), 1.23 (1H, m, H-19), 0.86 (3H, dd, J=7.3, 7.3 Hz, H$_3$-18).

$^{13}$C-NMR (100 MHz, CDCl$_3$) δ [ppm]: 169.1 (C-22), 160.3 (C-17), 157.0 (C-9), 149.6 (C-13), 129.3 (C-11), 117.6 (C-8), 111.9 (C-16), 106.0 (C-12), 102.1 (C-10), 82.8 (C-7), 63.7 (C-1'), 63.6 (C-2), 63.0 (C-3), 61.6 (17-OCH$_3$), 59.1 (C-21), 55.2 (9-OCH$_3$), 51.3 (22-OCH$_3$), 50.1 (C-5), 40.6 (C-20), 40.4 (C-15), 34.7 (C-14), 29.9 (C-3'), 26.2 (C-6), 22.9 (C-2'), 19.3 (C-19), 13.0 (C-18).

UV (MeOH) $\lambda_{max}$: 294.0, 241.0, 215.0 nm.

CD (0.219 mM, MeOH, 24° C.), λ nm (De): 338 (0), 300 (+0.5), 279 (0), 264 (−0.5), 245 (0), 236 (+0.5), 230 (0), 215 (−8.3).

EI-MS (%) m/z: 456 (M$^+$, 41), 73 (100).

HR-ESI-MS m/z: 457.27044 (MH$^+$, calcd. for C$_{26}$H$_{37}$N$_2$O$_5$, 457.27025).

Example 2

The analgesic actions of MGM-30 and MGM-29 synthesized in Example 1 were investigated. Details thereof are described below.

(Experimental Materials and Methods)

1. Animal

Six-week-old male ddY strain mice (Japan SLC, Inc.) were used.

2. Compounds

MGM-30 and MGM-29 were each dissolved in 25 mM phosphate buffer (pH 5.3 to 5.5). MGM-9, which was a known mitragynine derivative compound, was used as a sample for comparison. MGM-9 was obtained by synthesis according to a method similar to a method described in each of the previous reports (Patent Literatures 2 and 3 and Non Patent Literature 3).

3. Tail-Flick Test

A tail-flick test is a method of evaluating the analgesic effect of a compound, which comprises applying a nociceptive stimulus, for example, a heat stimulus, to the tail of a mouse, and then using as an indicator flight response elicited by the stimulus. Since a mouse respond to the heat stimulus by flicking or moving its tail out of the path of the stimulus, the tail is exposed to a photocell located in a tail-flick analgesia meter (Ugo Basile Tail-flick Unit 7360, Ugo Basile) immediately below the tail. A reaction time is automatically recorded.

Before treatment with the compounds, the vehicle, or physiological saline, a nociceptive threshold was measured three times, and the mean of the reaction time was used as a pre-drug latency for each mouse. The intensity of the heat stimulus was adjusted to such an intensity that mice flicked the tail upward within from 2 seconds to 4 seconds, and a time for heat treatment was set to a maximum stimulation time (cut-off time) of 10 seconds in order to prevent tissue damage. Each of the compounds was subcutaneously administered to mice in a volume of 10 mL/kg with doses 0.3 mg/kg, 1 mg/kg, and 3 mg/kg. A latency after the administration (post-drug latency) was measured 15 minutes, 30 minutes, 45 minutes, 60 minutes, 90 minutes, 120 minutes, and 180 minutes after the administration. The vehicle used for diluting the compounds was used as a control in place of the compounds, and was administered in the same volume. The analgesic action of each compound was quantified through use of a ratio to the maximum drug efficacy, i.e., a percentage of maximum possible effect (hereinafter abbreviated as % MPE) % MPE was calculated from the following equation: % MPE=[(Post-drug latency−Pre-drug latency)/(Cut-off time−Pre-drug latency)]×100. Each value is expressed as the mean of data obtained from six mice±standard error.

4. Statistical Analysis

Data was expressed as the mean±standard error. Statistical analyses were performed by the two-tailed Student's t test for comparison of two groups and by a one-way analysis of variance followed by a Bonferroni multiple-comparison test for comparison of more than two groups. A P value of <0.05 was considered statistically significant.

5. Results

Each of MGM-30, MGM-29, and MGM-9 exhibited a dose-dependent analgesic action by subcutaneous administration in the tail-flick test (FIG. 1). Among those compounds, MGM-30 exhibited the most potent analgesic action and had the longest duration of action.

Specifically, the maximum analgesic action of MGM-30 was expressed 15 minutes after the administration. In the administration at 1 mg/kg and 3 mg/kg, MGM-30 exhibited an analgesic action of 100% for a period of from 15 minutes to 60 minutes after the administration. The action was then reduced but was sustained until 90 minutes after the administration. In addition, even in the administration at 0.3 mg/kg, MGM-30 exhibited an analgesic action of about 95% for a period of from 15 minutes to 30 minutes after the administration. At any of the doses, 180 minutes after the administration, the analgesic action was returned to the same level as that in the administration of the vehicle.

Meanwhile, MGM-29 exhibited a limited analgesic action. That is, MGM-29 exhibited only an analgesic action of about 20% at 15 minutes after the administration at 3 mg/kg.

The maximum analgesic action of MGM-9 serving as the sample for comparison was expressed 15 minutes after the administration. MGM-9 exhibited an analgesic action of 100% at 15 minutes after the administration at 1 mg/kg and 3 mg/kg. In addition, in the administration at 3 mg/kg, MGM-9 exhibited an analgesic action of 100% for a period of from 15 minutes to 60 minutes after the administration. The action was then reduced but was sustained until 120 minutes after the administration. One hundred and eighty minutes after the administration, the analgesic action was returned to the same level as that in the administration of the vehicle.

Example 3

MGM-30 and MGM-29 synthesized in Example 1 were each evaluated for its metabolic stability and opioid receptor binding affinity. Details thereof are described below.

(Experimental Methods)

1. Evaluation of Metabolic Stability

Liver microsome was used and subjected to a reaction with MGM-30 or MGM-29 for a predetermined time. A sample subjected to the reaction was compared to a sample not subjected to the reaction to calculate a residual ratio for evaluating a degree of a compound that was metabolized in liver. MGM-9 was used as a sample for comparison and evaluated by the same method.

Commercially available pooled human liver microsome (manufactured by Xenotech) was used as human liver microsome. Pooled rat liver microsome prepared from rat liver by a method known per se was used as rat liver microsome.

A metabolic stability test was specifically performed as described below. First, a test compound was subjected to a reaction (oxidative reaction) at 37° C. for 0 minutes or 30 minutes in 0.2 mL of a buffer (50 mmol/L tris-HCl pH 7.4, 150 mmol/L potassium chloride, 10 mmol/L magnesium chloride) containing 0.5 mg protein/mL of liver microsome in the presence of 1 mmol/L nicotinamide adenine dinucleotide phosphate (hereinafter abbreviated as NADPH). After the reaction, 50 µL of the reaction liquid was added to 100 µL of a solution of methanol/acetonitrile=1/1 (volume/volume: hereinafter abbreviated as v/v), followed by mixing and centrifugation at 3,000 rpm for 15 minutes. The test compound in the centrifugation supernatant was quantified by liquid chromatograph/tandem mass spectrometry (LC/MS/MS). Then, the amount of the compound at the start of the reaction was defined as 100%, and the residual ratio of the test compound after the reaction was calculated. A hydrolysis reaction was performed in the absence of NADPH, and a glucuronidation reaction was performed in the presence of 5 mM UDP-glucuronic acid in place of NADPH. Then, the same operation was performed.

2. Evaluation of Binding Affinity to µ-Opioid Receptors

The binding of each of MGM-30 and MGM-29 to human µ-opioid receptors was evaluated through use of a µ-opioid receptor ligand DAMGO ([D-Ala(2), N-Me-Phe(4), Gly-ol (5)] enkephalin acetate salt). MGM-9 was used as a sample for comparison and evaluated by the same method.

A cell membrane fraction of CHO-K1 cells expressing human µ-opioid receptor gene (manufactured by PerkinElmer) was used as a reagent. The human µ-opioid receptor-expressing cell membrane fraction was diluted to 1 mg/mL or 100 µg/mL with 50 mM Tris-HCl (pH 7.4), and then 1 mL of the dilution was dispensed in each of screw-capped vials, cryopreserved at −80° C., and dissolved before use. DAMGO was prepared at 1 mM with dimethylsulfoxide (hereinafter abbreviated as DMSO), and then dispensed in each of screw-capped vials, cryopreserved at −20° C., and dissolved before use.

A human µ-opioid receptor binding test was performed through use of the human µ-opioid receptor-expressing cell membrane fraction and [$^3$H]-labeled DAMGO (DAMGO, [TYROSYL-3,5-3H], manufactured by PerkinElmer: hereinafter referred to as [$^3$H]-DAMGO). Specifically, 10 µL of [$^3$H]-DAMGO (final concentration: 1 nM) diluted to 50 nM with 50% ethanol was added to 10 µL of a test compound solution obtained by diluting each of MGM-30, MGM-29, and MGM-9 with DMSO so as to have a final concentration of from 0.1 nM to 10,000 nM. 480 µL of the µ-opioid receptor-expressing cell membrane fraction diluted to 40 µg/mL with binding assay buffer (10 mM MgCl$_2$, 50 mM Tris-HCl, 0.2% BSA, pH 7.4) was further added, followed by mixing, and the mixture was then subjected to a reaction at 27° C. for 2 hours. The same tests were performed for measurement of total binding activity by using 10 µL of DMSO in place of the test compound, and for measurement of µ-opioid receptor non-specific binding activity by using 10 µL of 1 mM DAMGO (final concentration: 20 µM) in place of the test compound. The binding reaction was terminated by suction filtration with a GF/C filter (manufactured by Whatman) preimmersed in 0.5% polyethylene imine. The filter was washed four times with 2.5 mL of a washing buffer (10 mM Tris-HCl, pH 7.4), and radioactivity remaining in the filter was measured. Then, a dissociation constant (Kd value) of [$^3$H]-DAMGO for the µ-opioid receptor-expressing cell membrane fraction was calculated by Scatchard plot analysis.

Data analysis was performed as described below. IC50 value was calculated, which is a test compound concentration at which the specific binding of [$^3$H]-DAMGO to human μ-opioid receptors was inhibited by 50%, by using analysis software XLfit™ (Microsoft, US). Then, an inhibition constant (Ki value) was calculated using the following equation: Ki=IC50/(1+S), S=(Concentration of [$^3$H]-DAMGO/Kd of [$^3$H]-DAMGO).

3. Results

The results of the metabolic stability test and the μ-opioid receptor binding test are shown in Table 1.

TABLE 1

| | Receptor Binding Test | | Metabolic Stability | |
|---|---|---|---|---|
| | hMOR binding Ki (nM) | hMOR agonist (% DAMGO) | Ms human (% remaining) | Ms rat (% remaining) |
| MGM-9 | 3.5 | 49.0 | 57 | 3 |
| MGM-29 | 4.9 | 45.9 | 78 | 36 |
| MGM-30 | 0.12 | 46.2 | 92 | 43 |

In Table 1, hMOR means human μ-opioid receptors, and Ms human and Ms rat mean human and rat liver microsomal fractions, respectively.

3-1. Results of Metabolic Stability Test

As shown in Table 1, the substrate residual ratios (stability) in human and rat liver microsomal fractions of MGM-30 and MGM-29, in both of which the cross-linking site at position 2 was converted into a carbon atom, were remarkably high as compared to those of MGM-9, which was a diether cross-linked product between position 2 and 7. Specifically, the substrate residual ratios in human and rat liver microsomal fractions were 57% and 3% for MGM-9, respectively, whereas the substrate residual ratios were 92% and 43% for MGM-30, respectively, and were 78% and 36% for MGM-29, respectively.

It is considered that the improvements in metabolic stability of MGM-30 and MGM-29 are attributed to the elimination of a chemically unstable hemiaminal structure between position 1 and position 2, which is contained in MGM-9, by the conversion of the cross-linked site at position 2 into a carbon atom When a drug is administered in vivo, the drug is degraded or metabolized in a process of migration thereof from an administration site to systemic circulation blood. As a result, an amount of the drug in migration decreases, and hence there are often observed cases in which the drug efficacy is reduced or not expressed. In the case of an oral formulation, a drug absorbed from small intestine migrates to systemic blood through liver via portal vein. However, a large number of metabolizing enzymes are present in liver, and hence some drugs are mostly metabolized therein (liver first-pass effect). Thus, the metabolic stability is an important factor for the expression of the drug efficacy of a drug in a body. It can be considered that a drug having higher metabolic stability has usefulness such as the expression of drug efficacy at lower dosage and a longer duration of drug efficacy.

As described above, each of MGM-30 and MGM-29 has high metabolic stability. This is considered to be a property extremely useful for the exhibition of an analgesic effect by an unchanged form thereof in a body.

3-2. Results of Binding Test for μ-Opioid Receptors

Each of MGM-30, MGM-29, and MGM-9 potently inhibited the binding of DAMGO to human μ-opioid receptors. As shown in Table 1, the Ki values of MGM-30, MGM-29, and MGM-9 for μ-opioid receptors were 0.12 nM, 4.9 nM, and 3.5 nM, respectively. That is, it was found that MGM-30 exhibited a binding affinity for human μ-opioid receptors about 30-fold as potent as that of MGM-9, while MGM-29 exhibited a binding affinity for human μ-opioid receptors comparable to that of MGM-9.

From the results, it is considered that each of MGM-30, MGM-29, and MGM-9 bound to μ-opioid receptors. It can also be considered that the strength of the binding decreases in the following order: MGM-30, MGM-9, and MGM-29, on the basis of the Ki values.

INDUSTRIAL APPLICABILITY

As described above, the compound according to the present invention exhibits an analgesic effect comparable to or more potent than that of morphine, and has higher metabolic stability, and hence is useful as a novel pharmaceutical product in a medical field in need of analgesic treatment, which is provided as a pharmaceutical agent and a pharmaceutical composition for analgesic treatment.

What is claimed is:

1. An analgesic, comprising a compound represented by the following formula (I) or the following formula (II) or a salt thereof, or a solvate thereof

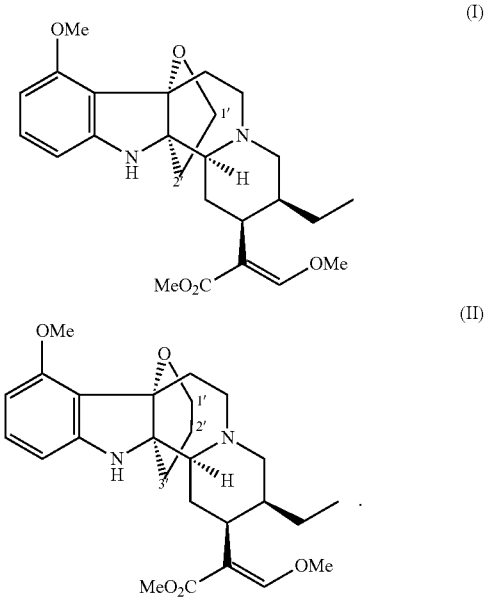

2. A pharmaceutical composition, comprising an effective amount of a compound of claim 1 and a pharmaceutical carrier.

3. The compound of claim 1 represented by the formula (I) or a salt thereof, or a solvate thereof.

4. The compound of claim 1 represented by the formula (II) or a salt thereof, or a solvate thereof.

5. A method of inducing an analgesic effect in a subject in need thereof, comprising administering an effective amount of the compound of formula (I) or formula (II) of claim 1 to the subject.

* * * * *